US008596270B2

(12) United States Patent
Chen et al.

(10) Patent No.: US 8,596,270 B2
(45) Date of Patent: Dec. 3, 2013

(54) SYSTEMS AND METHODS FOR CONTROLLING A VENTILATOR

(75) Inventors: Bo Chen, Louisville, CO (US); Edward M. McKenna, Boulder, CO (US)

(73) Assignee: Covidien LP, Mansfield, MA (US)

( * ) Notice: Subject to any disclaimer, the term of this patent is extended or adjusted under 35 U.S.C. 154(b) by 875 days.

(21) Appl. No.: 12/544,848

(22) Filed: Aug. 20, 2009

(65) Prior Publication Data

US 2011/0041849 A1 Feb. 24, 2011

(51) Int. Cl.
*A61M 16/00* (2006.01)
*A62B 7/00* (2006.01)
*F16K 31/02* (2006.01)
*A61B 5/00* (2006.01)

(52) U.S. Cl.
USPC ..................... 128/204.23; 600/323

(58) Field of Classification Search
USPC ............. 128/200.24, 203.12, 203.14, 203.25, 128/204.18, 204.21, 204.23, 204.26; 600/300, 301, 310, 323, 333, 483, 484
See application file for complete search history.

(56) References Cited

U.S. PATENT DOCUMENTS

| 5,315,990 | A | * | 5/1994 | Mondry | 128/205.11 |
|---|---|---|---|---|---|
| 5,682,877 | A | * | 11/1997 | Mondry | 128/204.23 |
| 5,682,898 | A | | 11/1997 | Aung et al. | |
| 6,599,251 | B2 | * | 7/2003 | Chen et al. | 600/485 |
| 6,702,752 | B2 | | 3/2004 | Dekker | |
| 6,760,608 | B2 | | 7/2004 | Lynn | |
| 6,848,444 | B2 | | 2/2005 | Smith et al. | |
| 6,930,608 | B2 | | 8/2005 | Grajales et al. | |
| 7,066,173 | B2 | | 6/2006 | Banner et al. | |
| 7,171,251 | B2 | | 1/2007 | Sarussi et al. | |
| 7,210,478 | B2 | | 5/2007 | Banner et al. | |
| 7,246,618 | B2 | | 7/2007 | Habashi | |
| 7,398,115 | B2 | | 7/2008 | Lynn | |
| 7,421,296 | B1 | | 9/2008 | Benser et al. | |
| 2001/0039951 | A1 | * | 11/2001 | Strickland, Jr. | 128/204.22 |
| 2002/0072659 | A1 | * | 6/2002 | Claure et al. | 600/323 |
| 2002/0112726 | A1 | * | 8/2002 | Schmidt et al. | 128/204.23 |
| 2004/0059209 | A1 | | 3/2004 | Al-Ali et al. | |
| 2005/0109340 | A1 | | 5/2005 | Tehrani | |
| 2005/0247311 | A1 | | 11/2005 | Vacchiano et al. | |
| 2006/0237015 | A1 | * | 10/2006 | Berthon-Jones et al. | 128/204.23 |
| 2006/0266355 | A1 | * | 11/2006 | Misholi | 128/204.23 |

(Continued)

FOREIGN PATENT DOCUMENTS

| EP | 0 996 358 | 5/2000 |
|---|---|---|
| EP | 1 790 283 | 5/2007 |

(Continued)

OTHER PUBLICATIONS

PCT International Search Report and the Written Opinion of the International Searching Authority, or the Declaration, Date of Mailing Oct. 29, 2010, Intl Application No. PCT/US2010/044950, Intl Filing Date: Aug. 10, 2010, Applicant: Nellcor Puritan Bennett LLC.

*Primary Examiner* — Oren Ginsberg
(74) *Attorney, Agent, or Firm* — Shvarts & Leiz LLP (57) ABSTRACT

A method and system for controlling a ventilator is disclosed. Oxygen saturation values from pulse oximeters may be used to adjust the settings of a ventilator. Multiple sensors and multiple oxygen saturation values in a fault tolerant pulse oximeter configuration may be used to provide a backup value or confidence measure, thereby increasing reliability and patient safety.

14 Claims, 5 Drawing Sheets

(56) References Cited

U.S. PATENT DOCUMENTS

| | | |
|---|---|---|
| 2007/0000494 A1 | 1/2007 | Banner et al. |
| 2007/0123785 A1 | 5/2007 | Lu et al. |
| 2007/0149871 A1 | 6/2007 | Sarussi et al. |
| 2007/0293746 A1 | 12/2007 | Sarussi et al. |
| 2008/0014115 A1 | 1/2008 | Johns |
| 2008/0066752 A1 | 3/2008 | Baker et al. |
| 2008/0076988 A1 | 3/2008 | Sarussi et al. |
| 2008/0076990 A1 | 3/2008 | Sarussi et al. |
| 2008/0076992 A1 | 3/2008 | Hete et al. |
| 2008/0202525 A1 | 8/2008 | Mitton et al. |
| 2008/0236582 A1 | 10/2008 | Tehrani |
| 2008/0295839 A1 | 12/2008 | Habashi |
| 2008/0314385 A1 | 12/2008 | Brunner et al. |
| 2009/0241954 A1* | 10/2009 | Karlsson ............. 128/204.23 |

FOREIGN PATENT DOCUMENTS

| | | |
|---|---|---|
| JP | 25034472 | 2/2005 |
| JP | 27167185 | 7/2007 |
| WO | WO-86/00234 A1 | 1/1986 |
| WO | WO-99/53834 A1 | 10/1999 |
| WO | WO-00/16839 A1 | 3/2000 |
| WO | WO-01/00264 A1 | 1/2001 |
| WO | WO-01/00265 A1 | 1/2001 |
| WO | 02/47741 A2 | 6/2002 |

* cited by examiner

SYSTEMS AND METHODS FOR CONTROLLING A VENTILATOR

The present disclosure relates to a medical ventilator system and, more particularly, the present disclosure relates to a medical ventilator system the operation of which depends at least in part on a patient's medical state.

SUMMARY

In the present disclosure, a pulse oximetry system is integrated with a ventilator system. The purpose is to use the oxygen saturation ($SpO_2$) reading generated by the pulse oximetry system to adjust the inspired oxygen level (e.g., $FiO_2$) being delivered by the ventilator (e.g., by changing any one or more appropriate settings of the ventilator to effect the desired $FiO_2$). However, the quality of the measurement resulting from a received oxygen saturation signal can be degraded by, for example, noise or sensor malfunction. In a critical care environment, a more reliable oxygen saturation reading is desired to increase patient safety.

By using multiple $SpO_2$ values in a fault tolerant pulse oximeter configuration, the reliability of the $SpO_2$ values used to calculate the ventilator settings may be increased, thereby increasing patient safety. Multiple $SpO_2$ values (e.g., two or more values) may be obtained through the use of a respective number of sensors attached to the patient. The pulse oximeter sensors may be placed at different locations on the patient (e.g., one on the left foot, one on the right foot). For example, multiple $SpO_2$ readings from one or more pulse oximeters may be used to determine how well the multiple $SpO_2$ signals match based on a predetermined criteria or threshold.

For example, the criteria for determining the ventilator settings may include calculating a difference between the multiple $SpO_2$ readings and comparing the difference to a threshold. Alternatively or in addition, the criteria for determining the ventilator settings may include comparing one or more of the multiple $SpO_2$ values to a threshold. Alternatively or in addition, the criteria for determining the ventilator settings may include comparing the multiple $SpO_2$ values to respective historical $SpO_2$ readings. If the multiple $SpO_2$ values meet the criteria, then one $SpO_2$ value may be output to the ventilator for controlling $FiO_2$ or an average of two or more of the multiple $SpO_2$ values may be calculated and provided to the ventilator system in determining an appropriate $FiO_2$. If the multiple $SpO_2$ values do not meet the criteria, the system may hold until an adequate $SpO_2$ signal is detected, or an average $SpO_2$ value may be output to the ventilator for controlling $FiO_2$. The average of the multiple $SpO_2$ values may be a weighted average with predetermined or dynamic weights.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

Ventilators mechanically move breathable air into and out of the lungs of a patient, providing the mechanism of breathing for a patient who is physically unable to breathe, or breathing insufficiently. In the present disclosure, a pulse oximetry system is integrated with a ventilator system. The purpose is to use the oxygen saturation ($SpO_2$) reading generated by of the pulse oximetry system to adjust the inspired oxygen level (e.g., $FiO_2$) of being delivered by the ventilator (e.g., by changing any one or more appropriate settings of the ventilator to effect the desired $FiO_2$). However, the quality of the measurement resulting from a received oxygen saturation signal can be degraded by, for example, electromagnetic coupling from other electronic instruments, movement of the patient, sensor malfunction, and environmental factors that interfere with the connection between the patient and the monitoring device. In a critical care environment, a more reliable oxygen saturation reading is desired to increase patient safety. A single sensor may be unable to provide the reliable output required to safely and properly adjust the inspired oxygen level of a ventilator.

By using multiple $SpO_2$ values in a fault tolerant pulse oximeter configuration, the reliability of the $SpO_2$ values used to calculate the ventilator settings may be increased, thereby increasing patient safety. Multiple $SpO_2$ values (e.g., two or more values) may be obtained through the use of a respective number of sensors attached to the patient. Multiple $SpO_2$ values allow for increased reliability over a single $SpO_2$ value by providing a backup value or a confidence measure. The pulse oximeter sensors may be placed at different locations on the patient (e.g., one on the left foot, one on the right foot). For example, if a first $SpO_2$ value exhibits signs of high noise interference (e.g., low signal quality), another $SpO_2$ value with a more reliable reading may be used instead to calculate the proper setting for a ventilator. As an alternative or in addition to the above, multiple $SpO_2$ values may be averaged to ensure the proper calculation of the ventilator setting. Various methods of using multiple $SpO_2$ values to calculate ventilator settings are discussed in further detail below.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda,t) = I_o(\lambda)\exp(-(s\beta_o(\lambda)+(1-s)\beta_r(\lambda))l(t)) \quad (1)$$

where:
$\lambda$=wavelength;
t=time;
I=intensity of light detected;
$I_o$=intensity of light transmitted;
s=oxygen saturation;
$\beta_o$, $\beta_r$=empirically derived absorption coefficients; and
l(t)=a combination of concentration and path length from emitter to detector as a function of time.

The traditional approach measures light absorption at two wavelengths (e.g., red and infrared (IR)), and then calculates saturation by solving for the "ratio of ratios" as follows.
1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_0 + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_0(\lambda_R) + (1-s)\beta_r(\lambda_R)}{s\beta_0(\lambda_{IR}) + (1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_0(\lambda_{IR}) - \beta_r(\lambda_{IR})) - \frac{d\log I(\lambda_{IR})}{dt}(\beta_0(\lambda_R) - \beta_r(\lambda_R))}$$

Note in discrete time $$\frac{d\log I(\lambda,t)}{dt} \simeq \log I(\lambda,t_2) - \log I(\lambda,t_1)$$

Using log A−log B=log A/B, $$\frac{d\log I(\lambda,t)}{dt} \simeq \log\left(\frac{I(t_2,\lambda)}{I(t_1,\lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1,\lambda_R)}{I(t_2,\lambda_R)}\right)}{\log\left(\frac{I(t_1,\lambda_{IR})}{I(t_2,\lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_0(\lambda_{IR}) - \beta_r(\lambda_{IR})) - \beta_0(\lambda_R) + \beta_r(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{dI/dt}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2,\lambda_R) - I(t_1,\lambda_R)}{I(t_1,\lambda_R)}}{\frac{I(t_2,\lambda_{IR}) - I(t_1,\lambda_{IR})}{I(t_1,\lambda_{IR})}} \quad (7)$$

$$= \frac{[I(t_2,\lambda_R) - I(t_1,\lambda_R)]I(t_1,\lambda_{IR})}{[I(t_2,\lambda_{IR}) - I(t_1,\lambda_{IR})]I(t_1,\lambda_R)}$$

$$= R$$

which defines a cluster of points whose slope of y versus x will give R where $$x(t) = [I(t_2,\lambda_{IR}) - I(t_1,\lambda_{IR})]I(t_1,\lambda_R)$$

$$y(t) = [I(t_2,\lambda_R) - I(t_1,\lambda_R)]I(t_1,\lambda_{IR})$$

$$y(t) = Rx(t) \quad (8)$$

Figure 1:
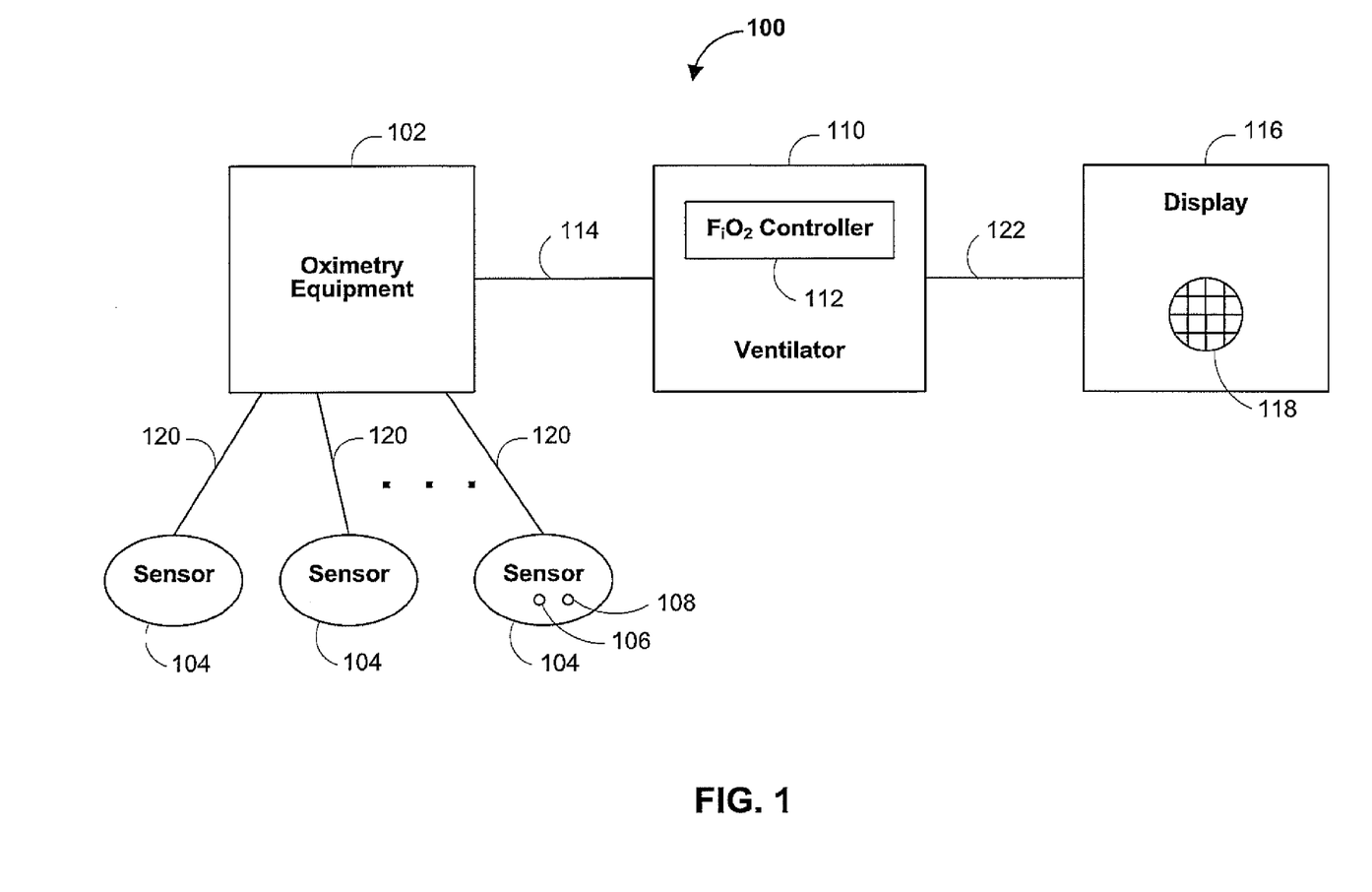
FIGS. 1 and 2 are block diagrams of illustrative ventilator systems in accordance with some embodiments.

FIG. 1 is a perspective view of an embodiment of a ventilator system 100 in accordance with some embodiments. According to an embodiment, system 100 may include oximetry equipment 102 and a plurality of sensors forming a sensor array 104. According to another embodiment, oximetry equipment 102 may include a plurality of pulse oximeters (not shown) with one or more sensors. Each of the plurality of pulse oximeters in oximetry equipment 102 may be communicatively coupled to the other pulse oximeters via cables (not shown). However, in other embodiments, a wireless transmission device (not shown) or the like may be used instead of or in addition to the cables.

Sensor 104 may include an emitter 106 for emitting light at two or more wavelengths into a patient's tissue. A detector 108 may also be provided in sensor 104 for detecting the light originally from the emitter 106 that emanates from the patient's tissue after passing through the tissue.

Each of the sensors 104 of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 106 and detector 108 may be on opposite sides of a digit such as a finger or toe, in which case the light that is emanating from the tissue has passed completely through the digit. In an embodiment, emitter 106 and detector 108 may be arranged so that light from emitter 106 penetrates the tissue and is reflected by the tissue into detector 108, such as a sensor designed to obtain pulse oximetry data from a patient's forehead.

In an embodiment, the sensors may be connected to and draw its power from oximetry equipment 102. In another embodiment, the sensors may be wirelessly connected to oximetry equipment 102 and include its own battery or similar power supply (not shown). Oximetry equipment 102 may be configured to calculate physiological parameters based at least in part on data received from sensors 104 relating to light emission and detection. In an alternative embodiment, the calculations may be performed on the monitoring device itself and the result of the oximetry reading may be passed to oximetry equipment 102.

In an embodiment, system 100 may include a ventilator 110. Ventilator 110 may be coupled to the patient via a nasal mask, a tracheotomy cannula, or any other suitable patient circuit for ventilation. Ventilator 110 may be powered by a battery (not shown) or by a conventional power source such as a wall outlet.

In an embodiment, system 100 may include an $FiO_2$ controller 104. In an embodiment, $FiO_2$ controller 104 may be incorporated in the same housing as ventilator 110 as shown in FIG. 1. Alternatively, $FiO_2$ controller 104 may be a part of oximetry equipment 102, or $FiO_2$ controller 104 may be an external or stand-alone component of system 100.

$FiO_2$ controller 104 may receive the patient's oxygen saturation data from oximetry equipment 102 to adjust the ventilation settings of ventilator 110. In an embodiment, the ventilator settings may include the fraction of inspired oxygen ($FiO_2$), tidal volume, respiratory rate, peak inspiratory flow rate, positive end-expiratory pressure (PEEP), any other suitable ventilator setting, or any combination thereof. In an embodiment, the ventilator settings may be machine commands to adjust the ventilator based on the calculated $FiO_2$, tidal volume, respiratory rate, peak inspiratory flow rate, PEEP, any other suitable ventilator setting, or any combination thereof.

In an embodiment, $FiO_2$ controller 104 may output $FiO_2$ settings to ventilator 110 and ventilator 110 may calculate the appropriate ventilator settings, or $FiO_2$ controller 104 may calculate the appropriate ventilator settings and output the ventilator settings to ventilator 110. It will be understood that the $FiO_2$ settings and/or ventilator settings may be calculated by $FiO_2$ controller 104, oximetry equipment 102, ventilator 110, any suitable processing device, or any combination thereof.

In an embodiment, ventilator 110 may be communicatively coupled to oximetry equipment 102 via cables 114. However, in other embodiments, a wireless transmission device (not shown) or the like may be used instead of or in addition to cables 114.

In an embodiment, system 100 may include a display 116 configured to display the physiological parameters or other information about the system. The display may include a cathode ray tube display, a flat panel display such as a liquid crystal display (LCD) or a plasma display, or any other type of display now known or later developed. Display 116 may be configured to provide a display of information from oximetry equipment 102, ventilator 110, $FiO_2$ controller 104, from other medical monitoring devices or systems (not shown) or any combination thereof. For example, display 116 may be configured to display an estimate of a patient's blood oxygen saturation generated by oximetry equipment 102 (referred to as an "$SpO_2$" measurement), pulse rate information from oximetry equipment 102, blood pressure from a blood pressure monitor (not shown), and ventilator settings from ventilator 110. In the embodiment shown, display 116 may also include a speaker 118 to provide an audible sound that may be used in various other embodiments, such as for example, sounding an audible alarm in the event that a patient's physiological parameters are not within a predefined normal range.

In an embodiment, sensors 104 may be communicatively coupled to oximetry equipment 102 via cables 120. However, in other embodiments, a wireless transmission device (not shown) or the like may be used instead of or in addition to cables 120.

Display 116 may be communicatively coupled to ventilator 110 via a cable 122 that is coupled to a sensor input port or a digital communications port, and/or may communicate wirelessly (not shown). Display 116 may be communicatively coupled to oximetry equipment 102 via a cable (not shown) that is coupled to a sensor input port or a digital communications port, and/or may communicate wirelessly. In addition, oximetry equipment 102, ventilator 110, and/or display 116 may be coupled to a network to enable the sharing of information with servers or other workstations (not shown). Display 116 may be powered by a battery (not shown) or by a conventional power source such as a wall outlet.

Figure 2:
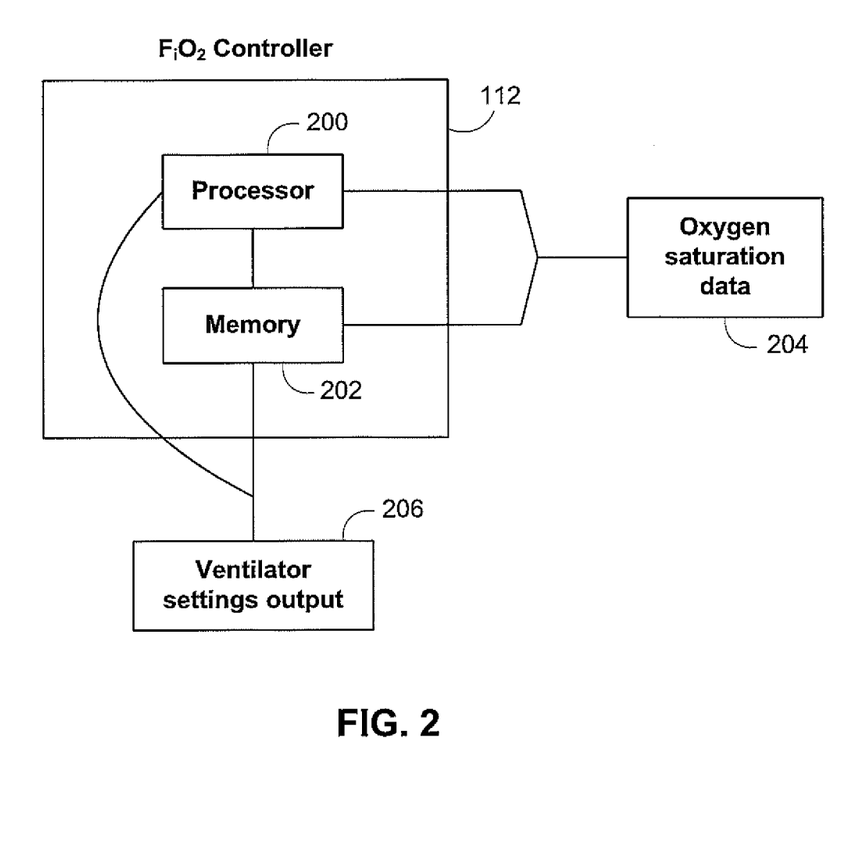

FIG. 2 is a block diagram of an $FiO_2$ controller, such as $FiO_2$ controller 112 of FIG. 1, in accordance with an embodiment. In an embodiment, processor 200 may be adapted to execute software, which may include an operating system and one or more applications, as part of performing the functions described herein. The data in $FiO_2$ controller 112 may be stored in a memory such as memory 202, which may be a read-only memory (ROM), a random access memory (RAM), or any suitable computer-readable media that may be used in the system for data storage. Computer-readable media are capable of storing information that can be interpreted by processor 200. This information may be data or may take the form of computer-executable instructions, such as software applications, that cause the processor to perform certain functions and/or computer-implemented tasks. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In an embodiment, processor 200 may receive from oximetry equipment 102 the patient's physiological parameters, such as oxygen saturation data 202, and calculate an output, such as ventilator settings output 206. Processor 200 may execute various processes and/or make use of look-up tables based on the value of the received signals and/or data corresponding to oxygen saturation data 202. In an embodiment, the real-time and historical oxygen saturation data 204 and the calculations of processor 200 may be stored in memory 202.

In an embodiment, oxygen saturation data 202 may contain information about sensor 104, such as what type of sensor it is (e.g., whether the sensor is intended for placement on a forehead or digit). Oxygen saturation data 202 may contain information specific to the patient, such as, for example, the patient's age, weight, and diagnosis. The information which may be included in oxygen saturation data 202 may allow processor 200 to determine ventilator settings output 206, as well as, for example, patient-specific threshold ranges in which the patient's physiological parameter measurements should fall and to enable or disable the determination of additional physiological parameters.

Oxygen saturation data 202 may include signal quality information. For example, low signal quality measurements may indicate that a patient is moving or that a sensor has malfunctioned, in which case measurements may be delayed or alternate sensor values may be used until a higher quality measurement can be obtained. Signal quality information may come from an electromagnetic noise measuring device (not shown) or a signal arising from sensor 104 indicating a malfunction or undesirable operating condition. In an embodiment, a visual display to indicate low signal quality may be shown on display 116, a audible alarm may be generated via speaker 118, any suitable alert may be generated, or any combination thereof. The signal quality information which may be included in oxygen saturation data 202 may allow processor 200 to determine ventilator settings output 206.

In an embodiment, ventilator settings output 206 may be retrieved from memory 202 and/or processor 200, and may be communicated to ventilator 110. In an embodiment, ventilator settings output 206 may contain an appropriate $FiO_2$ value for the patient and/or machine commands to ventilator 110 based on a calculated appropriate $FiO_2$ value.

Figure 3:
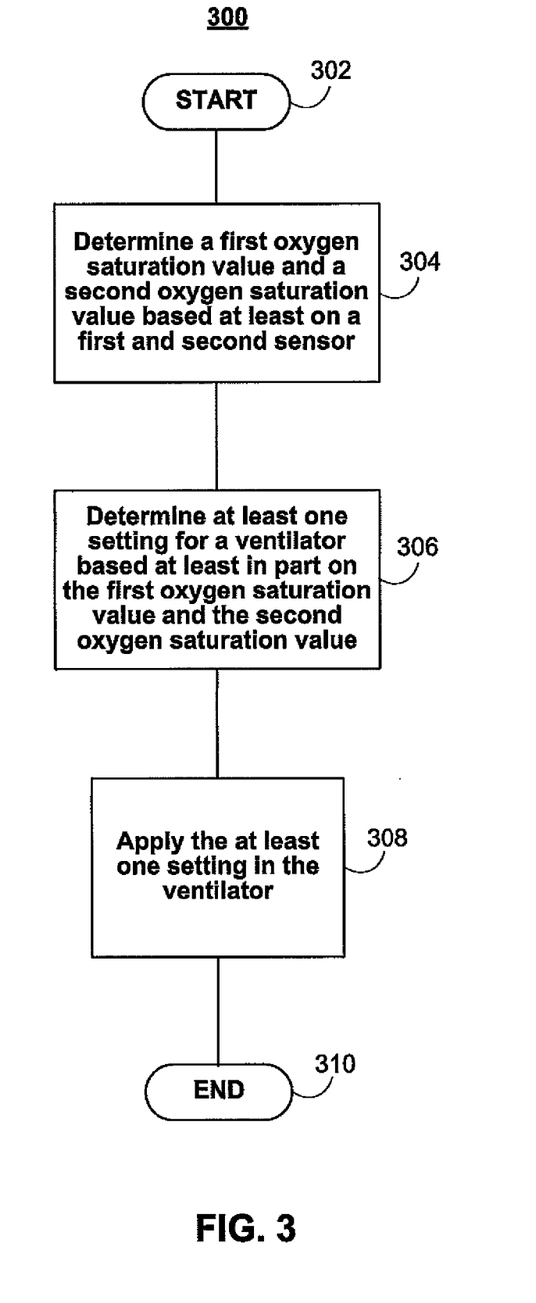
FIG. 3 is a flow chart of illustrative steps involved in controlling a ventilator in accordance with an embodiment.

FIG. 3 is a flow chart of illustrative steps involved in controlling a ventilator in accordance with some embodiments. Process 300 may begin at step 302. In an embodiment, at step 304, two or more oxygen saturation values (e.g., $SpO_2$ values) may be taken at about the same time based on respective signals (e.g., PPG signals) from two or more different sensors 104 coupled to one or more pulse oximeters in oximetry equipment 102, the sensors being attached to a patient (FIG. 1). It will be understood that, in some embodiments, a single pulse oximeter may be used having multiple channels each of which receives a respective sensor signal from the two or more sensors 104. In some embodiments, a single sensor may be used, the signal from which may be provided to two or more pulse oximeter devices (e.g., that are different models or use different $SpO_2$ calculation techniques) in order to provide the two or more respective $SpO_2$ values. For purposes of brevity and clarity, and not by way of limitation, the present disclosure shall refer to embodiments in which multiple sensors are used.

Multiple $SpO_2$ values allow for increased reliability over a single $SpO_2$ value by providing, for example, a backup value or a confidence measure. Each oxygen saturation value may be calculated using one or more signals that may be obtained from one or more sensors 104 or pulse oximeters in oximetry equipment 102. For purposes of brevity and clarity, and not by way of limitation, the signals from sensors 104 are described in the context of being PPG signals. In an embodiment, a PPG signal may be obtained from the patient using one or more sensors 104 in real time. In an embodiment, the PPG signal may have been stored in oximetry equipment 102 in the past and may be accessed by oximetry equipment 102 to be processed.

In an embodiment, at step 306, at least one setting for a ventilator may be determined based at least in part on the first and second oxygen saturation values. In an embodiment, the ventilator setting may be the fraction of inspired oxygen ($FiO_2$), tidal volume, respiratory rate, peak inspiratory flow rate, positive end-expiratory pressure (PEEP), any other suitable ventilator setting, or any combination thereof. In an embodiment, the ventilator setting may be machine commands to adjust the ventilator based on the calculated $FiO_2$, tidal volume, respiratory rate, peak inspiratory flow rate, PEEP, any other suitable ventilator setting, or any combination thereof.

In an embodiment, the ventilator setting may be determined by calculating a difference between two oxygen saturation values taken at about the same time based on respective PPG signals from two different sensors. For example, if the difference between the two oxygen saturation values is less than a threshold, the first oxygen saturation value may be used as the oxygen saturation metric (i.e., the oxygen saturation value used to calculate the ventilator setting). The threshold may be predetermined, dynamically calculated, inputted by a physician, or any combination thereof. If the difference is greater than a threshold, the first oxygen saturation value may be used as a default oxygen saturation metric. In the alternative, if the difference between the two oxygen saturation values is greater than a threshold, an average of the first and second saturation values may be used as the oxygen saturation metric used to calculate at least one ventilator setting. Alternatively, if the difference between the two oxygen saturation values is greater than a threshold, a historical oxygen saturation metric that was acceptable (e.g., where the difference between the oxygen saturation values was less than a threshold) may be used to calculate at least one ventilator setting. For purposes of brevity and clarity, and not by way of limitation, the calculations are performed in the context of two sensors and two oxygen saturation values. However, it will be understood that more than two sensors or oxygen saturation values may be used to determine the oxygen saturation metric.

In an embodiment, the ventilator setting may be determined by comparing to a threshold at least one of the two oxygen saturation values taken at about the same time based on respective PPG signals from two different sensors. The threshold may be predetermined, dynamically generated, inputted by a physician, or any combination thereof. For example, if both the first and second oxygen saturation values are less than a threshold, then the first oxygen saturation value may be used as the oxygen saturation metric used to calculate the appropriate ventilator setting. If only one of the oxygen saturation values is less than a threshold, then the oxygen saturation value that is less than the threshold may be used as the oxygen saturation metric used to calculate the appropriate ventilator setting. If both the first and second oxygen saturation values are greater than a threshold, the first oxygen saturation value may be used as a default oxygen saturation metric. In the alternative, if both the first and second oxygen saturation values are greater than a threshold, an average of the first and second saturation values may be used as the oxygen saturation metric used to calculate at least one ventilator setting. Alternatively, if both the first and second oxygen saturation values are greater than a threshold, a historical oxygen saturation metric that was acceptable (e.g., both oxygen saturation values were less than a threshold) may be used to calculate at least one ventilator setting. For purposes of brevity and clarity, and not by way of limitation, the calculations are performed in the context of two sensors and two oxygen saturation values. However, more than two sensors or oxygen saturation values may be used to determine the oxygen saturation metric.

In an embodiment, the ventilator setting may be determined by taking two oxygen saturation values taken at about the same time based on respective PPG signals from two different sensors and analyzing the change or trend of the oxygen saturation values in time. For example, a first change in the oxygen saturation value may be calculated by taking the difference between the first oxygen saturation value and a respective first previous oxygen saturation value, a second change in the oxygen saturation value may be calculated by taking the difference between the second oxygen saturation value and a respective second previous oxygen saturation value. In an embodiment, at least one of the first and second changes in oxygen saturation may be compared to a threshold. The threshold may be predetermined, dynamically generated, inputted by a physician, or any combination thereof. If the first and second changes in oxygen saturation are less than a threshold, then the first oxygen saturation value may be used as the oxygen saturation metric used to calculate the appropriate ventilator setting. If only one change in oxygen saturation is less than a threshold, then the oxygen saturation value with the change less than the threshold may be used as the oxygen saturation metric used to calculate the appropriate ventilator setting. If both the first and second changes in oxygen saturation value are greater than a threshold, the first oxygen saturation value may be used as a default oxygen saturation metric. In the alternative, if both the first and second changes in oxygen saturation value are greater than a threshold, an average of the first and second saturation values may be used as the oxygen saturation metric used to calculate at least one ventilator setting. Alternatively, if both the first and second changes in oxygen saturation value are greater than a threshold, a historical oxygen saturation metric that was acceptable (e.g., both oxygen saturation changes were less than a threshold) may be used to calculate at least one ventilator setting. For purposes of brevity and clarity, and not by way of limitation, the calculations are performed in the context of two sensors and two oxygen saturation values. However, more than two sensors or oxygen saturation values may be used to determine the oxygen saturation metric.

In an embodiment, an average of the oxygen saturation values may be used to determine an oxygen saturation metric suitable for calculating the ventilator setting. In an embodiment, the average may be a weighted average of the oxygen saturation values. The weights may be predetermined, dynamically generated, inputted by a physician, or any combination thereof. For example, the weights associated with each oxygen saturation value may be based on the signal quality information associated with each sensor—a higher weight may be associated with the oxygen saturation value with the better signal quality. Signal quality information may come from an electromagnetic noise measuring device or a signal arising from the sensor indicating a malfunction or undesirable operating condition.

It will be understood that averages, thresholds, any other suitable metric, or any combination thereof may be used to select or calculate an oxygen saturation metric for determining a ventilator setting.

Once the oxygen saturation metric is calculated, a ventilator setting may be determined using the oxygen saturation metric. For example, ventilatory support may be increased when the oxygen saturation metric indicates low oxygen saturation levels. Conversely, ventilatory support may be decreased as oxygen saturation levels increase, thus limiting the time at higher ventilation settings. In an embodiment, the ventilator setting may be the fraction of inspired oxygen ($FiO_2$), tidal volume, respiratory rate, peak inspiratory flow rate, positive end-expiratory pressure (PEEP), any other suitable ventilator setting, or any combination thereof. In an embodiment, the ventilator setting may be machine commands to adjust the ventilator based on the calculated $FiO_2$, tidal volume, respiratory rate, peak inspiratory flow rate, PEEP, any other suitable ventilator setting, or any combination thereof.

In an embodiment, at step 308, the ventilator setting calculated in step 306 may be outputted to the ventilator, such as ventilator 110 in FIG. 1. Ventilator 110 may accordingly adjust the oxygen delivered to a patient based on the ventilator setting determined above. Ventilator 110 may take the machine commands generated in step 306 above and adjust the mixture of air and oxygen flow to apply the calculated setting. In an embodiment, ventilator 110 may take the ventilator setting (e.g., the $FiO_2$ setting) and generate machine commands (e.g., via an $FiO_2$ controller such as $FiO_2$ controller 112 in FIG. 1) to adjust the mixture of air and oxygen flow to apply the calculated ventilator setting. Following the applying of the ventilator setting in step 308, process 300 may advance to step 310 and end.

Figure 4:
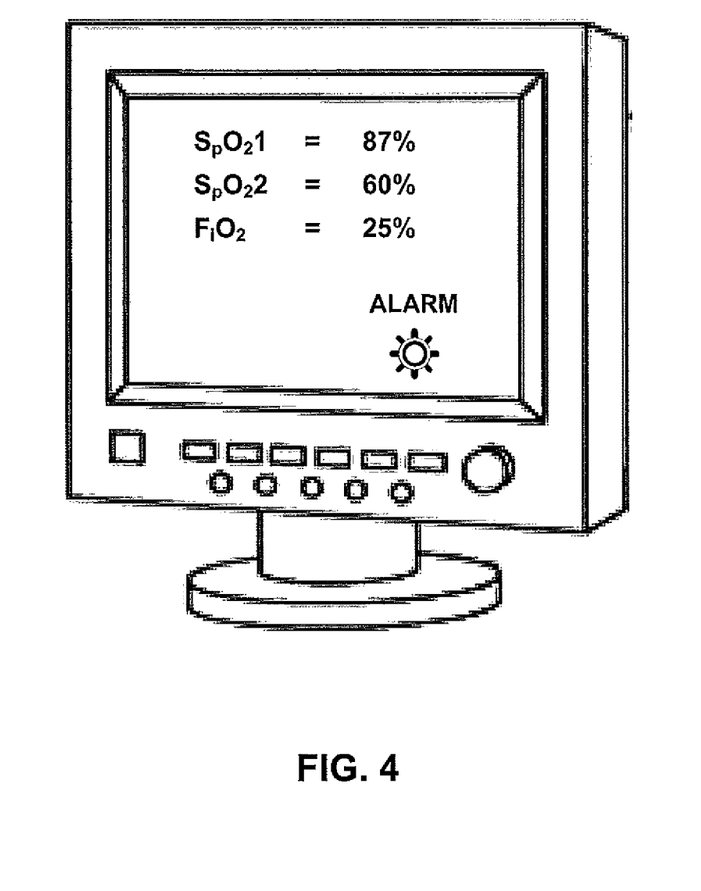
FIG. 4 shows an illustrative output device displaying ventilator settings and oxygen saturation values in accordance with an embodiment.

In an embodiment, the ventilator settings, the oxygen saturation values, any other parameter, or any combination thereof may be outputted to display 116 (FIG. 1) or any other display device communicatively coupled to system 100. For example, the oxygen saturation values may be displayed on a display as illustrated by FIG. 4. It will be understand that any other metric may be displayed to indicate the ventilator settings, oxygen saturation values, such as a status bar, a visual alarm, an audible alarm, any other suitable indication, or any combination thereof. For example, an audible and visual alarm may occur if the changes in oxygen saturation values are greater than a threshold as described above. The ventilator settings and oxygen saturation values may also be outputted to any other suitable output device, such as a computer, a computer-readable medium, a printer, any other suitable output device, or any combination thereof.

Figure 5:
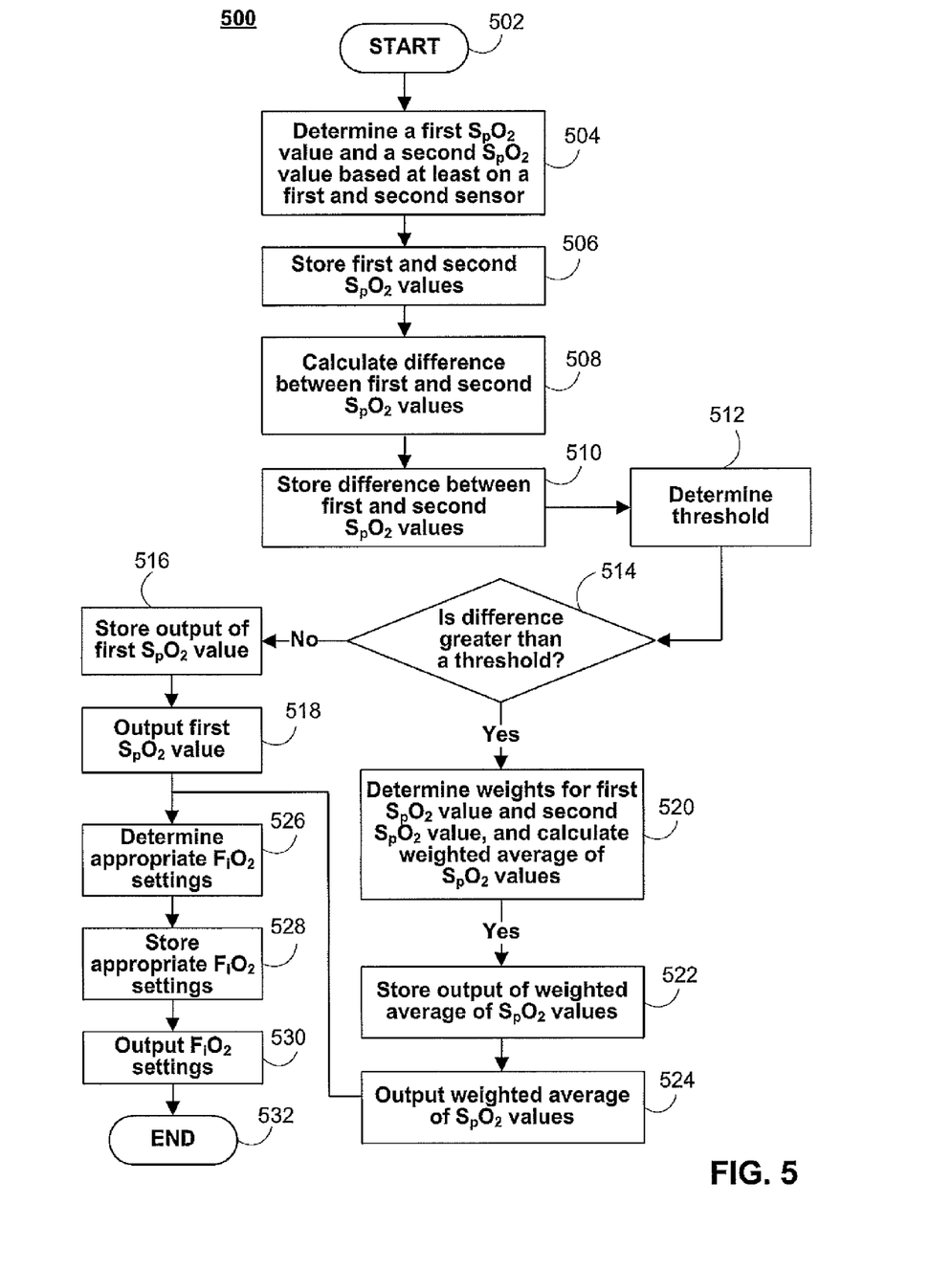
FIG. 5 is a flow diagram of illustrative steps involved in controlling a ventilator in accordance with an embodiment.

By way of illustration, FIG. 5 is a flow diagram of illustrative steps involved in controlling a ventilator in accordance with some embodiments. Process 500 may begin at step 502. In an embodiment, at step 504, oxygen saturation values (e.g., $SpO_2$ values) may be calculated using the signals (e.g., PPG signals) that may be obtained from sensors 104 that may be coupled to patient (FIG. 1). In an embodiment, the PPG signal may be obtained from the patient using sensors 104 in real time. In an embodiment, the PPG signal may have been stored in oximetry equipment 102 in the past and may be accessed by oximetry equipment 102 to be processed.

After receiving the signal at step 504, the first and second oxygen saturation values may be stored in processor 200 and/or memory 202 of FiO$_2$ controller 112 in step 506. At step 508, a difference between the first and second oxygen saturation values may be calculated. This difference may be stored in processor 200 and/or memory 202 of FiO$_2$ controller 112 in step 510.

In an embodiment, at step 512, a threshold may be determined. For example, a threshold may be input by a physician, retrieved from processor 200 or memory 202, or dynamically generated based on patient data. At step 514, the difference calculated in step 508 is compared to the threshold determined in step 512. If the difference is not greater than the threshold, process 500 moves to step 516, where the first oxygen saturation value may be stored in processor 200 and/or memory 202. At step 518, the first oxygen saturation value stored in step 516 may be output to ventilator 110.

If the difference is greater than the threshold in step 514, process 500 moves to step 520. At step 520, weights may be determined for each of the first and second oxygen saturation values determined in step 504. For example, the signal quality information of sensors 104 may be used, increasing the weight of the oxygen saturation value with better signal quality. After determining the weights, a weighted average of the first and second oxygen saturation values is calculated. At step 522, the weighted average of the oxygen saturation values is stored in processor 200 and/or memory 202. At step 524, the weighted average of the oxygen saturation values stored in step 522 may be output to ventilator 110.

At step 526, the output oxygen saturation metric of step 518 or step 524 may be used to determine an appropriate FiO$_2$ setting for the ventilator. This calculation may be performed by ventilator 110 or FiO$_2$ controller 112. The calculations performed by ventilator 110 or FiO$_2$ controller 112 may be designed to adjust the FiO$_2$ levels, within limits, to respond to patient needs. For example, ventilator 110 or FiO$_2$ controller 112 may increase FiO$_2$ support when the patient develops low oxygen saturation. Conversely, the FiO$_2$ controller 112 may decrease FiO$_2$ support as the patient improves, thus limiting the time at higher FiO$_2$ settings. The appropriate FiO$_2$ levels may be calculated, for example, based at least in part on the following equations:

$$FiO2_i = FiO2_{i-1} + G_{err}*(Sat_{target} - Sat_i) + G_{der}*(Sat_{i-1} - Sat_i)$$

$$FiO2_i = \min(1.0, FiO2_i)$$

$$FiO2_i = \max(0.21, FiO2_i)$$

$$G_{err} = 0.25$$

$$G_{der} = 0.01$$

where:
FiO2$_i$=current FiO$_2$ setting;
FiO2$_{i-1}$=previous FiO$_2$ setting;
Sat$_{target}$=target SpO$_2$ value;
Sat$_i$=current SpO$_2$ value; and
Sat$_{i-1}$=previous SpO$_2$ value.

The FiO$_2$ setting may be stored in processor 200 and/or memory 202 in step 528. The calculated FiO$_2$ setting may be output to ventilator 110 in step 530, and ventilator 110 may adjust the amount of oxygen delivered to the patient. Following the output of the FiO$_2$ setting, process 500 may advance to step 532 and end. In practice, one or more of the steps shown in processes 700 may be combined with other steps, performed in any suitable order, performed in parallel (e.g., simultaneously or substantially simultaneously), or removed.

The foregoing is merely illustrative of the principles of this disclosure and various modifications can be made by those skilled in the art without departing from the scope and spirit of the disclosure.

What is claimed is:

1. A method for controlling a ventilator in communication with a patient, the method comprising:
   calculating a first oxygen saturation value based at least in part on a first signal generated by a first sensor attached to the patient;
   calculating a second oxygen saturation value based at least in part on a second signal generated by a second sensor attached to the patient;
   determining with processing equipment at least one setting for the ventilator based at least in part on the first oxygen saturation value and the second oxygen saturation value, wherein the determined at least one setting comprises a fractional inspired oxygen setting of the ventilator; and
   applying the at least one setting.

2. The method of claim 1, wherein the determining comprises calculating a difference between the first oxygen saturation value and the second oxygen saturation value.

3. The method of claim 1, wherein the determining comprises determining whether at least one of the first oxygen saturation value and the second oxygen saturation value is greater than a threshold.

4. The method of claim 1, wherein the determining comprises:
   calculating a first change in the oxygen saturation of the patient by taking the difference between the first oxygen saturation value and a respective first previous oxygen saturation value;
   calculating a second change in the oxygen saturation of the patient by taking the difference between the second oxygen saturation value and a respective second previous oxygen saturation value; and
   determining whether at least one of the first change and the second change is greater than a threshold.

5. The method of claim 1, wherein the determining comprises calculating an average of the first oxygen saturation value and the second oxygen saturation value.

6. The method of claim 5, wherein the average is a weighted average and wherein the first oxygen saturation value and the second oxygen saturation value are associated with predetermined respective weights.

7. The method of claim 5, wherein the average is a weighted average and wherein the first oxygen saturation value and the second oxygen saturation value are associated with dynamic respective weights.

8. The method of claim 1, wherein applying the setting comprises modifying the fractional inspired oxygen setting of the ventilator.

9. A non-transitory computer-readable medium for controlling a ventilator, the non-transitory computer-readable medium having computer program instructions recorded thereon for:
   calculating a first oxygen saturation value based at least in part on a first signal generated by a first sensor attached to a patient;
   calculating a second oxygen saturation value based at least in part on a second signal generated by a second sensor attached to the patient;
   determining with processing equipment at least one setting for the ventilator based at least in part on the first oxygen saturation value and the second oxygen saturation value, wherein the determined at least one setting comprises a fractional inspired oxygen setting of the ventilator; and applying the at least one setting.

10. The non-transitory computer-readable medium of claim 9, wherein the determining comprises calculating a difference between the first oxygen saturation value and the second oxygen saturation value.

11. The non-transitory computer-readable medium of claim 9, wherein the determining comprises determining whether at least one of the first oxygen saturation value and the second oxygen saturation value is greater than a threshold.

12. The non-transitory computer-readable medium of claim 9, wherein the determining comprises:
- calculating a first change in the oxygen saturation of the patient by taking the difference between the first oxygen saturation value and a respective first previous oxygen saturation value;
- calculating a second change in the oxygen saturation of the patient by taking the difference between the second oxygen saturation value and a respective second previous oxygen saturation value; and
- determining whether at least one of the first change and the second change is greater than a threshold.

13. The non-transitory computer-readable medium of claim 9, wherein the determining comprises calculating an average of the first oxygen saturation value and the second oxygen saturation value.

14. The non-transitory computer-readable medium of claim 9, wherein applying the setting comprises modifying the fractional inspired oxygen setting of the ventilator.

* * * * *